(12) United States Patent
Nistor

(10) Patent No.: US 8,153,427 B2
(45) Date of Patent: Apr. 10, 2012

(54) CARDIOMYOCYTES AND METHODS OF PRODUCING AND PURIFYING CARDIOMYOCYTES

(75) Inventor: Gabriel Nistor, Placentia, CA (US)

(73) Assignee: California Stem Cell, Inc., Irvine, CA (US)

( * ) Notice: Subject to any disclaimer, the term of this patent is extended or adjusted under 35 U.S.C. 154(b) by 499 days.

(21) Appl. No.: 12/050,050

(22) Filed: Mar. 17, 2008

(65) Prior Publication Data

US 2009/0155831 A1     Jun. 18, 2009

Related U.S. Application Data

(60) Provisional application No. 60/895,066, filed on Mar. 15, 2007.

(51) Int. Cl.
*C12N 5/071* (2010.01)
*C12Q 1/02* (2006.01)

(52) U.S. Cl. .......... 435/377; 435/29; 435/325; 435/373

(58) Field of Classification Search ........................ None
See application file for complete search history.

(56) References Cited

U.S. PATENT DOCUMENTS

| 7,449,334 B2 * | 11/2008 | Thomson et al. ............. 435/377 |
| 7,767,643 B2 * | 8/2010 | Brines et al. ...................... 514/8 |
| 2007/0204351 A1 * | 8/2007 | Davidson et al. .................. 800/3 |

FOREIGN PATENT DOCUMENTS

| WO | 2005/056779 A1 | 6/2005 |
| WO | 2007/070964 A1 | 6/2007 |

OTHER PUBLICATIONS

Castro-Obregon et al. FEBS Letters, 1996, vol. 381. No. 1-2, pp. 93-97.*
Kehat et al. Nature Biotechnology. 2004, vol. 22, No. 10, pp. 1282-1289.*
Dimarakis, I., et al., In Vitro Stem Cell Differentiation Into Cardiomyocytes Part 2: Chemicals, Extracellular Matrix, Physical Stimuli and Coculture Assays, Journal of Cardiothoracic-Renal Research, 1:115-121 (2006).
Filipczyk, A.A., et al., Regulation of Cardiomyocyte Differentiation of Embryonic Stem Cells by Extracellular Signalling, Cell Mol. Life Sco, 64:704-718 (2007).
Moretti, A., et al., Biology of Isl1+ Cardiac Progenitor Cells in Development and Disease, Cell. Mol. Life Sci., 64:674-682 (2007).
Mummery, C., et al., Differentiation of Human Embryonic Stem Cells to Cardiomyocytes Role of Coculture With Visceral Endoderm-Like Cells, Circulation, 107:2733-2740 (2002).
Passier, R., Increased Cardiomyocyte Differentiation from Human Embryonic Stem Cells in Serum-Free Cultures, Stem Cells, 23:772-780 (2005).
Van Laaake, L.W., et al., Cardiomyocytes Derived from Stem Cells, Annals of Medicine, 37:499-512 (2005).
Dimarakis, I. et al., "In Vitro Stem Cell Differentiation into Cardiomyocytes Part 1. Culture Medium and Growth Factors", Journal of Cardiothoracic-Renal Research, Sep. 2006, 7 pgs, vol. 1:No. 2, Elsevier Ltd., Amsterdam, Netherlands, pp. 107-114.

* cited by examiner

*Primary Examiner* — Vera Afremova
(74) *Attorney, Agent, or Firm* — Baker & Hostetler LLP; Mark H. Krietzman

(57) ABSTRACT

The invention provides methods for producing a culture of cardiomyocytes and cultures of cardiomyocytes. Exemplary methods of producing and cultures of cardiomyocytes include a population of cells including cells having spontaneous and periodic electrical activity, and/or including nodal, sino-atrial or pacemaker cells; immature cardiomyocytes (cardiomyoblasts); mature contractile cardiomyocytes; or a mixed population of two or more of such cells.

19 Claims, 7 Drawing Sheets

CARDIOMYOCYTES AND METHODS OF PRODUCING AND PURIFYING CARDIOMYOCYTES

RELATED APPLICATIONS

Figure 1:
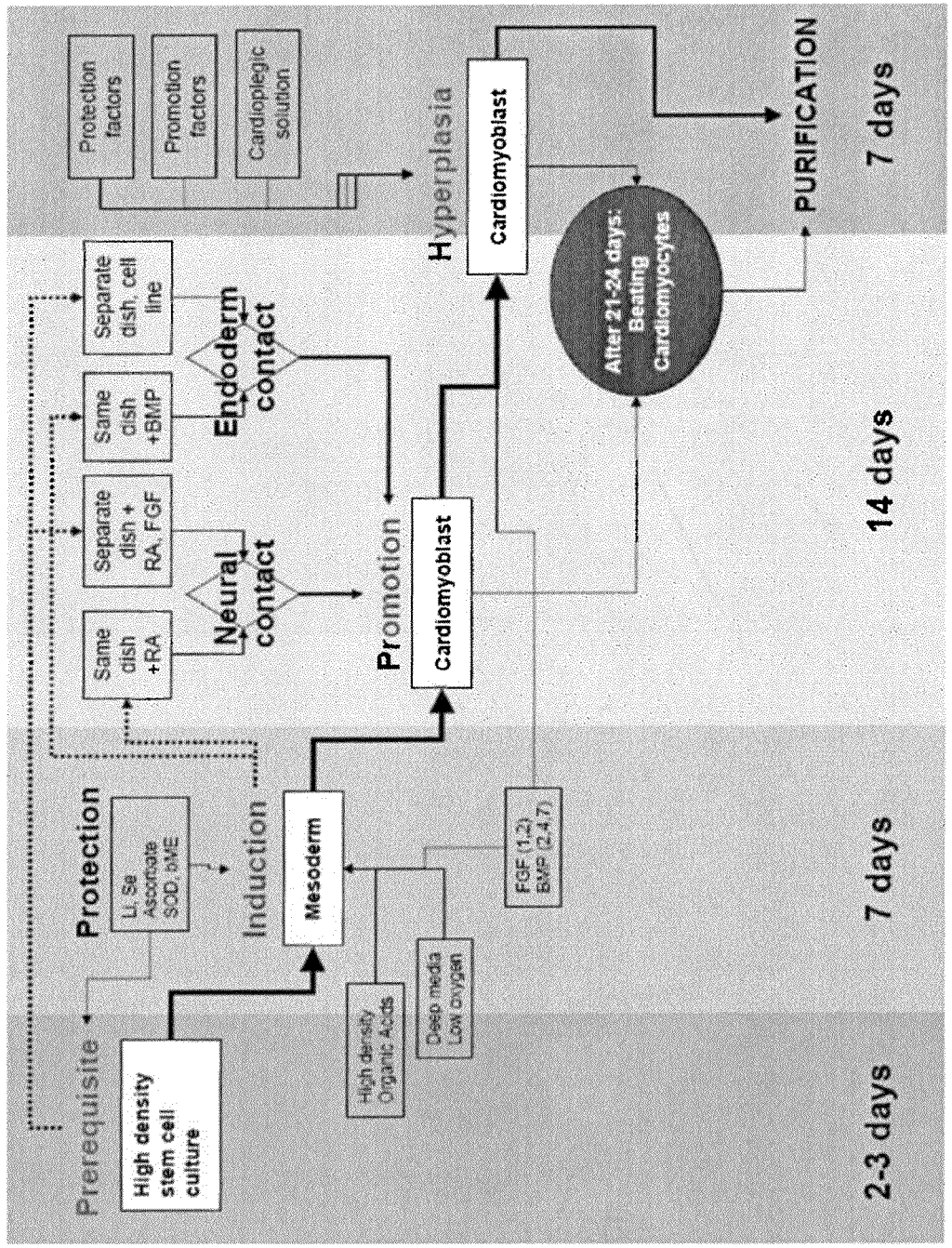

This application claims the benefit or priority of U.S. application Ser. No. 60/895,066, filed Mar. 15, 2007, and is expressly incorporated herein by reference.

INTRODUCTION

Myocardic Development

As the embryo is growing thicker than 300-400 microns, the diffusion of nutrients, oxygen, and carbon dioxide is inadequate. A circulatory system is needed and developed by the middle of the fourth week of gestation (embryonic day 24). Heart and skeletal muscle progenitor cells are derived from distinct regions of the mesoderm: lateral plate mesoderm and paraxial mesoderm, respectively. Cells from the cranial paraxial mesoderm (anterior splancnic mesoderm) contribute to both myocardial and endocardial cell populations. The primordium of the heart forms in the cardiogenic plate located at the cranial end of the embryo.

Development of the Conduction System

The factor that directs myocardial development toward either a working myocardium phenotype or a conduction system phenotype is not known. On the basis of positional clues, neural crest cells might play a role in the induction of the central conduction system and for the epicardium-derived cells in differentiation of the Purkinje network. These neural crest cells present as a central mass of condensed mesenchyme between the fourth and sixth pharyngeal arch arteries and extend two prongs deep down into the proximal cushions. This phenomenon was first described in the avian embryo and confirmed in human embryos during the fusion of the cushions from distal to proximal.

Growth Factors and Pathways Involved in Cardiac Development

Bone morphogenic protein 4 and 2 (BMP4, BMP2) induces cardiac differentiation in the cranial paraxial mesoderm, and blocks the differentiation of skeletal muscle precursors in these cells. Bone morphogenic proteins belong to the transforming growth factor beta super family (TGF-beta). Ligand binding to its receptor induces the formation of a complex in which the Type II BMP receptor phosphorylates and activates the Type I BMP receptor. The Type I BMP receptor then propagates the signal by phosphorylating a family of signal transducers, the Smad proteins. Currently, eight Smad proteins have been cloned (Smad 1-7 and Smad 9). Upon phosphorylation by the BMP Type I receptor, Smad1 can interact with either Smad4 or Smad6. The Smad1-Smad6 complex is inactive; however, the Smad1-Smad4 complex triggers the expression of BMP responsive genes. The ratio between Smad4 and Smad6 in the cell can modulate the strength of the signal transduced by BMP. BMP signaling is regulated at different molecular levels, most important—Noggin and other cystine knot-containing BMP antagonists bind with BMP-2, 4 and 7 and block BMP signaling. If activated, Smad6 binds type I BMP receptor and prevents Smad 1, 5 and 8 to be activated. The BMP family comprises: BMP1, BMP2, BMP3, BMP4, BMP5, BMP6, BMP7, BMP8a, BMP8b, BMP10, BMP15. The most important factors involved in the cardiac development are BMP2, BMP4, BMP7 and BMP10.

Wnt-mediated signals from the underlying neural tube and notochord suppress cardiomyocyte specification. Wnt proteins form a family of highly conserved secreted signaling molecules that regulate cell-to-cell interactions during embryogenesis. Wnt proteins bind to receptors of the Frizzled and LRP families on the cell surface. Through several cytoplasmic relay components, the signal is transduced to b-catenin, which then enters the nucleus and forms a complex with TCF to activate transcription of Wnt target genes. To date, there are at least 19 known Wnts in human, spread over 10 chromosomes. The Wnts involved in mesodermal and cardiac development are: Wnt-2b/13; Wnt-3/Int-4; Wnt-3a; Wnt-8a/8d.

Inhibitors of Wnt family (Crescent, Dkk-1, and glycogen synthase kinase-3) determine a gradient along the cardiogenic area (lateral mesoderm and anterior endoderm). Administration of exogenous crescent or Dkk-1 to posterior lateral plate mesoderm induces heart muscle formation while repressing erythropoiesis. Conversely, ectopic expression of either Wnt-8c or Wnt-3a in precardiac mesoderm blocks cardiogenesis in this tissue while promoting formation of primitive erythrocytes.

Cripto signaling primes differentiation of embryonic stem cells into cardiomyocytes and inhibits neural differentiation of ES cells. Cripto is a member of the CFC-EGF family of both secreted and membrane anchored proteins. Cripto mediates the binding of Nodal, Vg1, and GDF1 to the activin receptors. Failure to activate Cripto signaling results in conversion of ES cells into a neural fate. EGF-CFC domain (epidermal growth factor-Cripto/FRL-1/Cryptic coreceptors) alone is sufficient for Cripto activity in the cardiogenic induction.

TGFβs, Activin, Nodal, and Vg1/GDF1 are ligands for EGF-CFC coreceptors and potent mesendoderm inducers in vertebrates.

Endothelin-1 (ET-1) is an endothelium-derived peptide with potent vasoconstrictor and proliferative properties. It is involved in the conduction system development.

The gradient of BMP (BMP2, BMP4, BMP7) signaling can be regulated with ligand traps: DAN, Cerberus, Chordin/SOG, Follistatin, Noggin.

Markers for Myocardic Development

Nkx2.5/Csx is first expressed in the presumptive precardiac mesoderm, and is later restricted to the bilateral dorsal regions that will develop into the muscular portions of the heart, which is maintained throughout development. The number of cells in the cardiac conduction system is directly related to Nkx2-5 gene dosage. Nkx2.5 mutations are associated with conduction system abnormalities in both mouse and man. Transcription factors that are expressed during cardiac development include, for example, a GATA binding family transcription factor (GATA binding protein, such as GATA 4), MEF2 (Myocyte Enhancer Factor 2), HAND (heart and neural crest derivatives), Irx, Tbx, and HRT families of transcription factors. Additional factors include, for example, SRF (serum response factor), Isl1 (Islet1), LIM (named from the Lin-11, Isl-1 and Mec-3 genes) and alpha-actin.

SUMMARY

The invention provides methods for producing a culture of cardiomyocytes. In one embodiment, a method includes: providing a culture of stem cells that are at least 90% confluent or the cells have overgrown to form multiple layers of cells, or proliferating stem cells until the cells are at least 90% confluent or the cells have overgrown to form multiple layers of cells; inducing formation of mesoderm by contacting the overgrown stem cells with a bone morphogenic protein (BMP) receptor ligand and an fibroblast growth factor (FGF) receptor ligand for a period of about 2 to 15 days; and promoting cardiomyocyte formation by contacting mesoderm cells with neural cells or endoderm cells, or a neural cell or endoderm cell conditioned culture supernatant, for a period of about 1 to 21 days, thereby producing a culture of cardiomyocytes. In particular methods embodiments, cardiomyocytes comprise a population of cells including cells having spontaneous and periodic electrical activity, and/or including nodal, sino-atrial or pacemaker cells; immature cardiomyocytes (cardiomyoblasts); mature contractile cardiomyocytes; or a mixed population of two or more of such cells.

The invention also provides cardiomyocytes at any developmental, maturation or differentiation stage. Such cells are indicated at the various time points in Table 1, and can represent a mixed population of cells at a particular developmental, maturation or differentiation stages or a relatively uniform population of cells in which a majority of cells (e.g., 50%, 60%, 70%, 80%, 90% or more) is at a particular developmental or maturation type or stage. Such cells therefore include cells having spontaneous and periodic electrical activity, and/or including nodal, sino-atrial or pacemaker cells; immature cardiomyocytes (cardiomyoblasts); mature contractile cardiomyocytes; or a mixed population of two or more of such cells. Such cells include progenitor cells and precursor cells of the cells indicated at the various time points in Table 1, as well as daughter cells arising from the cells indicated at the various time points in Table 1. In particular embodiments, a cell culture includes immature cardiomyocytes (cardiomyoblasts), wherein 50% or more (e.g., 60%, 70%, 80%, 90%, etc.) of said culture comprises immature cardiomyocyte (cardiomyoblast) cells. In additional particular embodiments, a cell culture includes immature cardiomyocytes (cardiomyoblasts) in which no more than about 30% (e.g., no more than about 25%, 20%, 15%, 10%, 5%, etc.) of said cells beat or contract.

DRAWING DESCRIPTIONS

FIG. 1 shows a flowchart of cardiomyocyte production and purification.

Figure 2A:
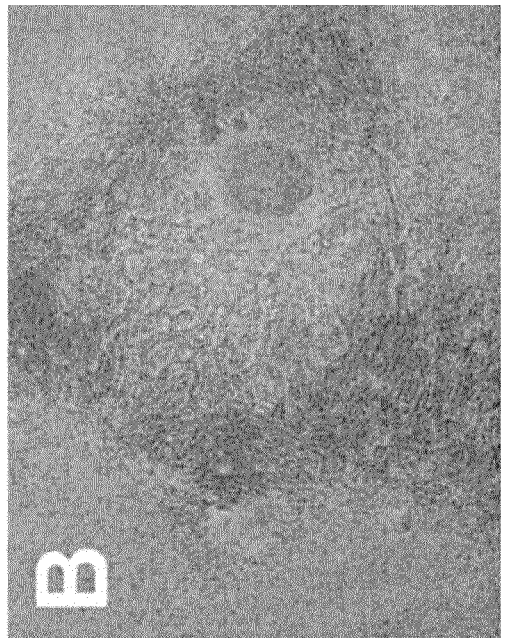
Figure 2B:
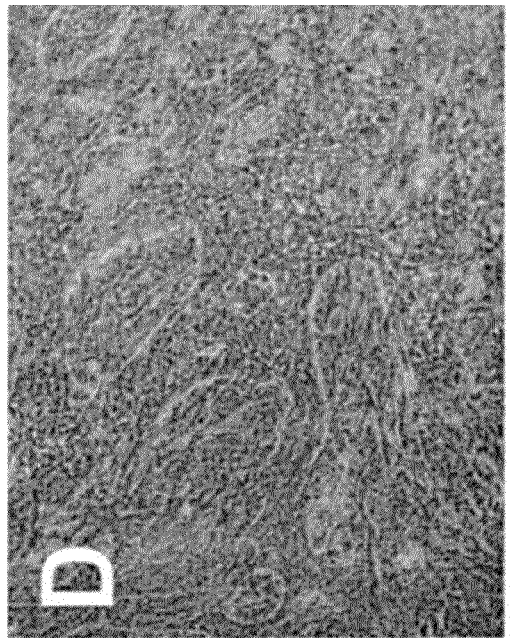
Figure 2C:
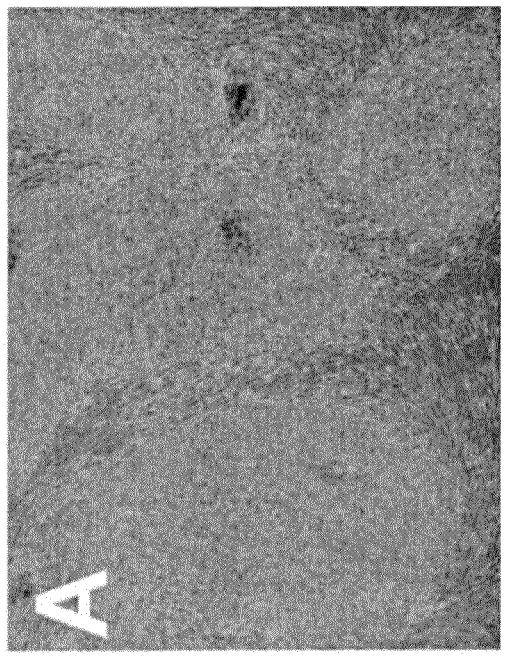
Figure 2D:
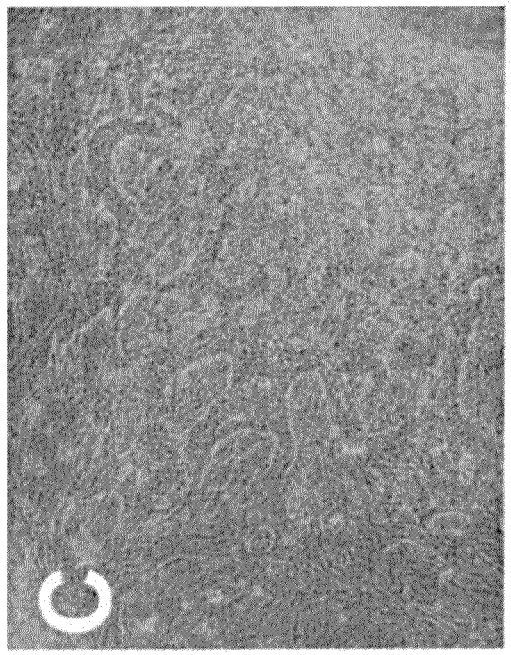

FIGS. 2A-2C show A) High density stem cell culture prior induction; B) cardiomyocyte colony, centered by nodal tissue and surrounded by less differentiated mesodermal population; and C) cardiomyocytes organized in syncytial trabeculy. Less differentiated cardioblasts between the organized cardiomyocytes.

Figures 3A, 3B:
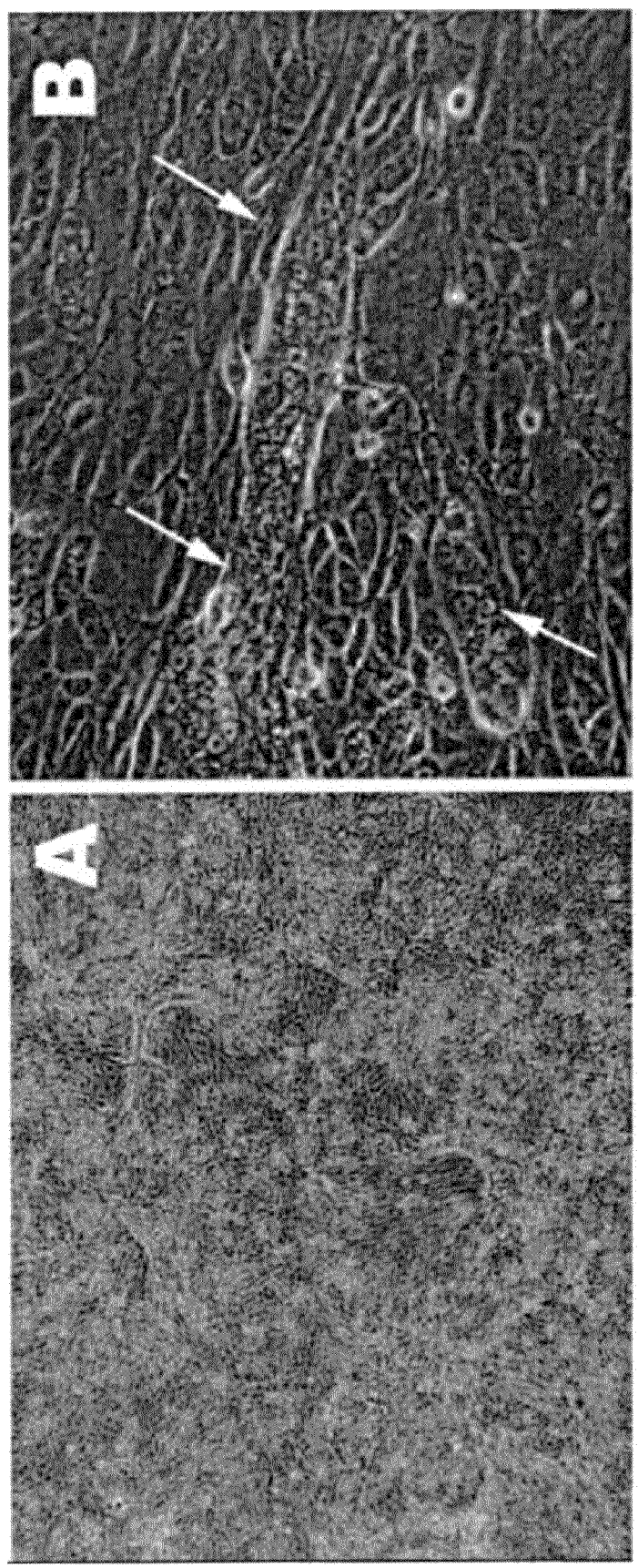
Figures 3C, 3D, 3E:
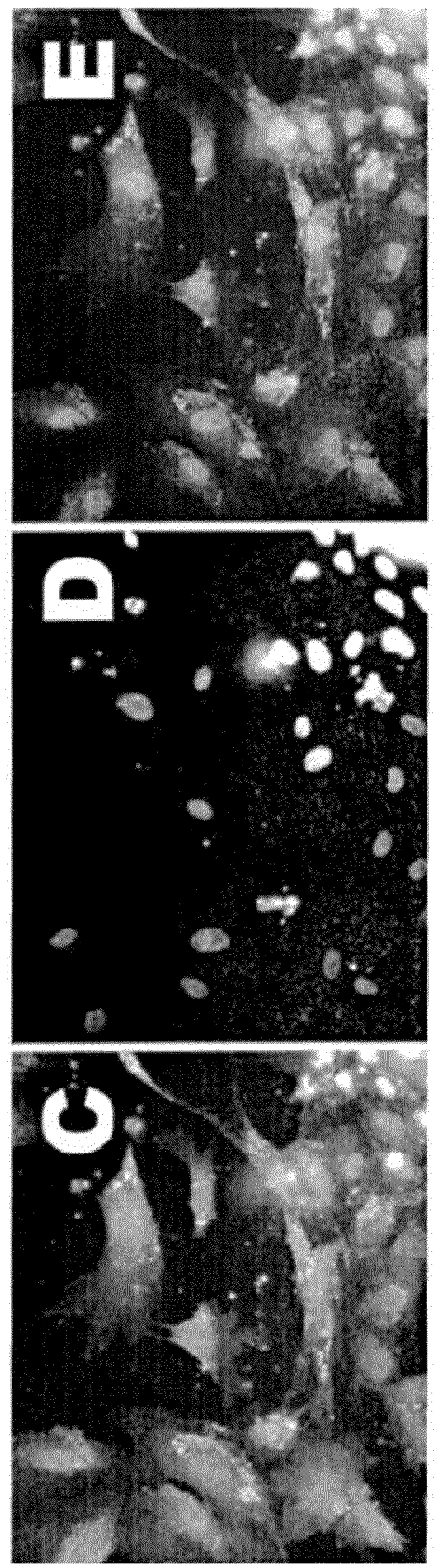
Figures 3F, 3G, 3H:
Figures 3I, 3J, 3K:
Figures 3L, 3M, 3N:
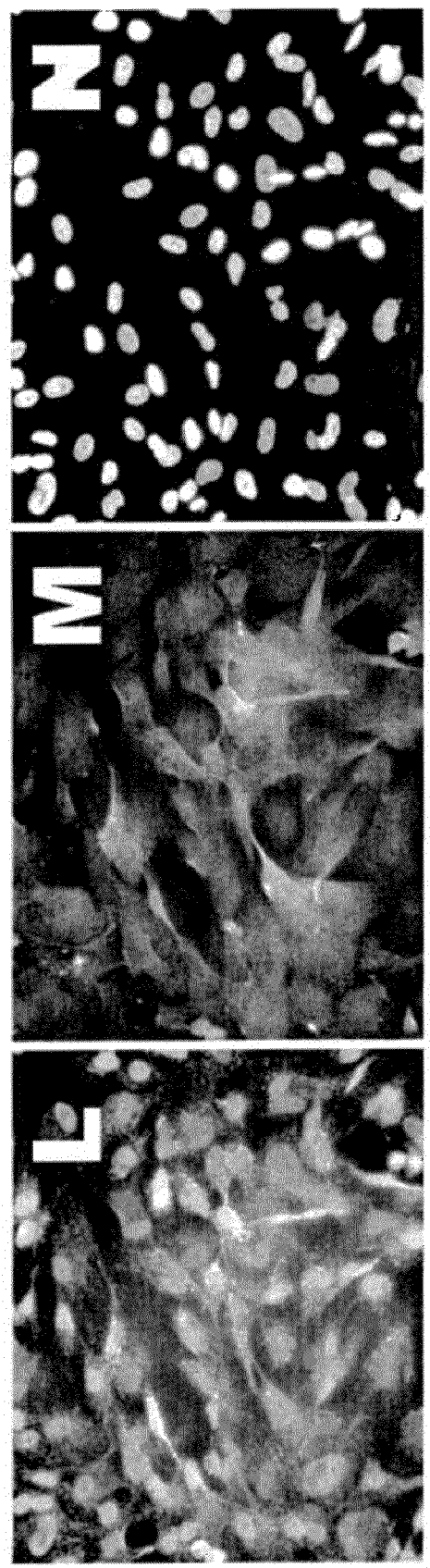

FIGS. 3A-3N show cardiomyoblasts after growth under certain conditions for certain periods of time: A) Homogenous growth of cardiomyoblasts in a 18 day old culture showing formation pf trabecular clusters; B) syncitial structures (arrows) after 21-24 days of differentiation; C) cardiomyocyte cultures can be dissociated and replated on adherent substrate at earlier stages, when NKX2.5 transcription factor is present; D) Nuclear staining with bisbenzimide; E) merged pictures; F) mature myocardial cells fuse and form trabecular structures positive for a-actin; G) bisbenzimide nuclear stain; H) merged picture. (60×); I) actin labeling persists after enzymatic dissociation of the cultures; J) nuclear stain with bisbenzimide; K) Merged picture (20×); L) and M) Colabeling with NKX2.5 (L) and actin (M), shows the overall expression of NKX2.5, while the actin is progressively expressed; N) Nuclear counterstain (100×).

DETAILED DESCRIPTION

Expansion of stem cells is important in early stage since priming can affect outcome. Priming is a slight tendency of the stem cell culture to differentiate towards ecto- or endoderm. Since cardiac tissue has a mesodermal origin, a good balance between ectoderm and endoderm populations is indicative of successful differentiation. A healthy stroma, defined as the cells resulting from spontaneous differentiation in an ES cell culture, is a good differentiation prognostic. The fibroblastic shaped cells surrounding the colonies typically have clear cytoplasm without vacuoles, little or nor membrane fragmentation and little or no tendency for detachment from substrate. An ectoderm dominance can be recognized if adjacent to stem cell colonies extensive epithelial plaques or small triangular cells are observed. An endoderm dominance is shown by polygonal cell with abundant cytoplasm, mostly growing in the center of the colonies.

Induction creates conditions in which differentiation of stem cells is pushed toward mesoderm. Balancing the FGF/Wnt signals with the opposite BMP favors the development of cardiac tissue. Induction can be accomplished in various ways.

Exemplary physical conditions include growth of stem cell cultures to high density, hypoxia and acidosis. One way is to grow the cultures without splitting over the passage point, e.g., with over 90% or more, or 100% confluency. Non discriminative counts (including the stem cells and stromal cells) are typically greater than about 150,000 cells/cm2 to 250,000 cells/cm2. The stroma appears dense, and the colonies tend to form multilayers, as observed by a rough, yellow color on top of the cells. Following stem cell over growth, acidosis and hypoxic conditions will develop in the culture. A pH decrease alternatively can be accomplished optionally using organic acids (e.g., lactic, citric, fumaric, ascorbic, folic, malic, succinic, oxalacetic, ketoglutaric acids, etc.) to a pH value of not less than about 6.5-6.8. Hypoxia can be accomplished in incubators with a low oxygen concentration (0.5 to 2%) and a deeper supernatant (5 mm to 10 mm) (recommended). The media can then be replaced with a new formulation. Appropriate basal media include. For example, MEM, DMEM, F12 and mixtures thereof. Optional supplements include, for example, glucose, B27 supplement, albumin (e.g., human), essential and non essential aminoacids, Glutamax 1× or L-Glutamine 1×, a thyroid hormone (e.g., T3/4, 20 ng/ml), insulin (e.g., 10 ug/ml), transferrin, ethanolamine, sodium selenite, a hydrosoluble vitamin, and a liposoluble vitamin.

Signaling can be used to induce cardiomyogenesis. Exemplary signaling is two or more signals used to induce cardiomyogenesis, for example, a ligand for FGF receptor and a ligand for BMP receptor. The signals can be added to the culture from exogenous sources or secreted by coculture or supernatant from specialized cells. Ligands for the FGF receptor include, for example, FGF basic (FGF2, bFGF). Other members of the FGF family can be used (for example FGF1). The amount the FGF is typically about 5 to 20 ng/ml but can be extended from 2 to 200 ng/ml. Ligands for the BMP receptors include, for example, BMP4. Other BMPs can be used, for example BMP2, BMP7 or a combination. The BMPs are typically used at a concentration of about 0.5 to 10 ng/ml, but can be from 0.1 to 100 ng/ml.

A Wnt family member may also be optionally used in conjunction with above factors in cell cultures. One example of a Wnt family member is Wnt-5a (e.g., at a concentration of 1 to 10 ng/ml).

Induction is accomplished by exposing the stem cells to one or more of the above physical conditions and signaling factors for 3 to 10 days, typically for about 7 days. During induction, growth conditions (hypoxia, acidosis) will cause extensive cellular loss. Inhibition or prevention of cell death (protection) can be accomplished using selenium (for example, sodium selenite) at a concentration of about 1 to 20 ng/ml (0.5 to 50 ng/ml), lithium (for example, lithium carbonate) at a concentration of about 1-20 ng/ml (0.5-50 ng/ml); ascorbic acid or ascorbate (for example sodium or calcium ascorbate) 1 ug/ml (0.1 to 20 ug/ml); superoxide dismutase (SOD) 1-10 u/ml (1-100 u/ml). These and other protective elements can be used in combination, for increased efficacy. Each individual component is optional; typically a combination of two is used.

After induction to promote development of cardiomyocytes, for about the next 10-14 days, signaling which promotes the cardiomyocyte development can be maintained by exposing the cell culture to other cell populations known as a source of signal factors. This cell population can be placed in the same culture dish or cultured separately and the supernatant media used to feed the cardiac cells. The other cell populations that can be used include neural cells, which can spontaneously or be directed to differentiate in the same culture, for example, by addition of retinoic acid (e.g., 1-20 mMol or 5-10 mMol). Alternatively, cardiomyocyte media can be incubated overnight (e.g., 12-48, or about 24 hours) on pre-differentiated or primary neural cultures or neural progenitor cultures. Endodermal cells can develop in the same culture dish with the cardiomyocytes after exposure to BMPs. Alternatively, a separate culture of endodermal cells from differentiated embryonic stem cell or a primary culture of endo-epithelial cells could also be used to condition the cardiomyocyte media for a period of time (e.g., 12-48, or about 24 hours).

During promotion of cardiomyogenesis other factors which stimulate cellular metabolism, division and growth (proliferation) can be added to enrich (increase numbers) the cardiomyocyte population. Non limiting examples include insulin (e.g., 5 to 50 µg/ml, 15 µg/ml), thyroid hormones (e.g., T3/4, 1 to 40 ng/ml, 20 ng/ml) and IGF (e.g., 5-50 ng/ml, 10 ng/ml).

After about 21 to 28 days of growth, beating (contractile) cellular conglomerates are typically observed. Beating (contractile) frequency varies with the media pH, temperature, and responds to various cardiomodulator drugs (e.g., catecholamine, calcium blockers, potassium)

Contracting (beating) cardiomyocytes tend to terminally differentiate and undergo cell cycle arrest. A cardioplegic solution or treatment can protect cardiomyocytes by inducing a rapid diastolic arrest, minimizing energy requirements and inhibiting or preventing hypoxic damage during purification. A mixture which includes a membrane stabilizer and/or a Ca channel inhibitor is an example of a cardioplegic solution, which can be added as needed (e.g., daily to feeding media). Particular components of such a mixture include KCl (e.g., 10-20 mM), $MgCl_2$ (e.g., 10 mM), $CaCl_2$ (e.g., 1.2 mM), puerarin (e.g., 0.5 mM), Nifedipine (a calcium channel inhibitor that prevents intracellular Ca accumulation, e.g., 1-10 u/ML), tromethamine (e.g., Tris) buffer (e.g., 0.3 M) adjusted to a pH of about 8.6, L-Monosodium Glutamate Monohydrate, L-Monosodium Aspartate Monohydrate or a mixture of L-Monosodium Glutamate Monohydrate (e.g., 4.277%), L-Monosodium Aspartate Monohydrate (e.g., 3.923%). The components are mixed, sterile filtered and typically used in 5% to 50% v/v dilution with growth media.

For purification, one optional method for selection of cardiomyocytes is by identification of beating colonies. With the use of an ablator laser (XY Clone, Zeiss etc) or manually surrounding cells or the colonies are removed in separate dishes. Another method uses the ability of the cardiomyocyte to switch to anaerobic metabolism, while the other cells in the culture that aerobically metabolize are killed. In particular, for example, exposure to absolute hypoxia and exposure to lactic acid in cardioplegic solution for about 30-60 minutes.

After purification, cells can be recovered using media enriched with cardioplegic mixture and dissociated and re-plated in new dishes coated with an adherent substrate to expand cells. Hyperplasia can follow for about another week and purification can be repeated before dissociation. If the cardioplegic mixture is removed from media, the cardiomyocytes should restart contractile (beating) activity shortly.

For preservation in diastolic arrest, cardiomyocytes can be cryopreserved and stored indefinitely in liquid nitrogen. Freezing can be done after dissociation, or with cells attached to culture plates. If intended for transportation involving a limited time (e.g., 1-12 hours), diastolic arrest in conjunction with hypothermia (e.g., +4 C to +30 C) can be employed without cryopreservation.

Cardiomyocytes, at different developmental stages, can be used for various applications. Two particular applications are in vitro drug testing and in vivo cell replacement therapy. Mature cardiomyocytes with syncytial morphology and contractile activity are suitable for in vitro drug testing or screening. These cells tolerate fewer manipulations and are recommended not to be dissociated.

Cardioblasts, immature cardiomyocytes can be used for transplant as cellular replacement therapy. Such cells can be collected beginning from the promotion phase of differentiation, and stored frozen after cryopreservation. Atrial/pacemaker cells from the central areas of the cardiomyocyte colonies, can be used for pacemaker cellular replacement in vivo.

Table 1 provides an overview of conditions, media, cardioplegic treatment, factors and other components, cell markers and morphologic features at the various stages of cardiomyocyte production, characterization and isolation. Populations of cells at any of the various time points in Table 1 can be isolated, purified or expanded, or provided as a cell culture or kit or other composition. The invention therefore provides isolated and purified cells at each of the various time points, as well as a cell culture or kit or other composition that includes cells at each of the various time points, as well as daughter cells derived therefrom (undergo subsequent proliferation, maturation, development or differentiation into additional cells).

Populations of cells at various time points in Table 1 can represent a mixed population of cells at different developmental, maturation or differentiation stages or a relatively uniform population of cells in which a majority of cells (e.g., 50%, 60%, 70%, 80%, 90% or more) is at a particular developmental or maturation type or stage. Populations of cells at various time points in Table 1 can also be maintained at that stage, in other words, development or maturation of one or more cell types within the population generally is arrested at a particular stage, such that the cells remain in at the stage (e.g., cardioblasts). Such cells can be expanded (proliferate) while maintaining the cells at a particular developmental, maturation or differentiation stage, or can be released (unlocked) to mature or further develop or differentiate, in accordance with the invention.

TABLE 1

| | Prerequisite | Induction | Promotion | Hyperplasia | Purification |
|---|---|---|---|---|---|
| Time | 0-3 days | 7 days | 14 days | 7 days | 1-2 day |
| Physical conditions | Attached, mesodermal stroma. No tendencies toward ecto or endoderm differentiation | Attached to substrate, Hyperconfluency, 100%-150%, Cellular stress: deep media 5-20 mm, hypoxia (Oxygen <5-2%) and acidosis (pH 7.0-7.2) | Attached Feeding accordingly to cellular density, reduced cellular stress | Attached Feeding accordingly to cellular density, reduced cellular stress | Attached on substrate Hypoxia <2% for 30-60 min |
| Media composition | Stem cell media | Cardio media | Cardio media | Cardio media + Cardioplegic mixture (when contractile colonies observed) | Cardio media + Cardioplegic mixture + Lactic acid (for 30-60 min) |
| Protection | No | Selenite, Lithium, Ascorbate, Superoxyde Dismutase (SOD), bMercaptoEthanol | Selenite Lithium SOD, bMercaptoEthanol | Selenite Lithium SOD, bMercaptoEthanol | After 30-60 min of exposure: Selenite Lithium SOD, bMercaptoEthanol |
| Growth factors | FGF 10 ng/ml | FGF 10 ng/ml BMP4 (and/or 2, 7) 1-5 ng/ml | FGF 2 (and/or FGF1) - 5-10 ng/ml BMP4 (and/or 2, 7) 1-5 ng/ml | FGF 2 (and/or FGF1) - 5-10 ng/ml | After recovery FGF 2 (and/or FGF1) - 5-10 ng/ml |
| Optional components | | Organic acids; lactic, citric, ascorbic, piruvic. Concentration adjusted to media pH not lower than 6.8 RA (10 uM) for 3 days if mixed neural exposure is decided | Media incubated over night on neural cultures if RA not used at induction (separate neural exposure) Noggin 1-20 ng/ml alternative to neural exposure Thyroid hormones: 5-10 ng/ml IGF 10 ng/ml | Media incubated overnight on neural cultures if RA not used at induction Noggin 1-20 ng/ml alternative to neural exposure Thyroid horm: 5-10 ng/ml IGF 10 ng/ml | Piruvic acid Ascorbic acid Thyroid hormones: 5-10 ng/ml IGF 10 ng/ml |
| Macroscopic characterization | Delimited colonies, with fibroblastic stroma | Layering observed in hyperdense culture, media with phenol red colored yellow before feeding. Colonies delimited poorly, mesodermal transformation of the stem cells | Dense cellular agglomerations with prominent center (umbilicated). Toward the end of the period, the cellular agglomerations will initiate spontaneous beating | In cardioplegic solution no beating colonies should be observed and the colonies should progressively increase in size | The cells surrounding the cardiomyocyte colonies should be progressively eliminated |
| Markers | Oct4, SSEA4, Tra1-81, PA | Nkx2.5, MEF2, HAND, Isl1, LIM | + a-actin, ultrastructure | + a-actin, ultrastructure | |

In accordance with the invention, methods for producing a cell culture of cardiomyocytes are provided. In one embodiment, a method includes contacting stem cells with a bone morphogenic protein (BMP) receptor ligand and a fibroblast growth factor (FGF) receptor ligand for a period of about 2 to 15 days to induce mesoderm cells; and contacting mesoderm cells with neural cells or endoderm cells, or a neural cell or endoderm cell conditioned culture supernatant, for a period of about 1 to 21 days, thereby producing a cell culture of cardiomyocytes. In another embodiment, a method includes providing a culture of overgrown stem cells or proliferating stem cells until the cells are overgrown; contacting the overgrown stem cells with a bone morphogenic protein (BMP) receptor ligand and an fibroblast growth factor (FGF) receptor ligand for a period of about 2 to 15 days to induce formation of mesoderm; and contacting mesoderm cells with neural cells or endoderm cells, or a neural cell or endoderm cell conditioned culture supernatant, for a period of about 1 to 21 days, thereby producing a culture of cardiomyocytes.

Cardiomyocytes in one aspect, comprise a population of cells having spontaneous and periodic electrical activity. Cardiomyocytes in another aspect, include nodal, sino-atrial or pacemaker cells; immature cardiomyocytes (cardiomyoblasts); mature contractile cardiomyocytes; or a mixed population thereof. Such populations of cardiomyocytes can be maintained for a period of time (e.g., 1-24 minutes, hours, days, weeks, etc.) at a given developmental, maturation or differentiation stage, can be expanded or can be allowed to progress to a subsequent developmental, maturation or differentiation stage.

Stem cells of the methods and compositions of the invention include cells, such as cells of a cell monolayer with greater than about 60%, 70%, 80%, 90%-95% or more confluency (e.g., 96%, 97%, 98%, etc. . . . 100%). Overgrown cells are cell cultures greater than 100% confluency that form multiple layers of cells. Stem cells of the methods and compositions of the invention also include overgrown cells, such as cells that form a multilayer culture. Stem cells of the methods and compositions of the invention also include overgrown cells, such as cells having a density of about 150,000 to about 250,000 cells/cm$^2$.

Methods for producing a cell culture of cardiomyocytes, as well as cell populations of cardiomyocytes include addition of an acid. Exemplary non-limiting examples include lactic, citric, fumaric, ascorbic, folic, malic, succinic, oxalacetic, or ketoglutaric acid.

Methods for producing a cell culture of cardiomyocytes, as well as cell populations of cardiomyocytes include subjecting mesoderm cells to hypoxia, or having a cell population of cardiomyocytes which have been subjected to hypoxia. In particular aspects, the stem cells, mesoderm cells or cardiomyocytes are subjected to or are contained or comprised within an oxygen concentration of about 0 to 2.0%, such as cell cultures including cardiomyocytes in which such cells have been treated or subjected to hypoxia (e.g., 0%-2% oxygen). Degassing of growth medium to reduce or remove ambient or dissolved oxygen is typically performed when cells are subjected to hypoxia or treated with an agent that induces or stimulates hypoxia.

Methods for producing a cell culture of cardiomyocytes, as well as cell populations of cardiomyocytes further include addition of an agent, treatment or condition that inhibits cell death or apoptosis. In various aspects, an agent includes selenium (e.g., sodium selenite), lithium (e.g., lithium carbonate); ascorbic acid or ascorbate (e.g., sodium or calcium ascorbate) or superoxide dismutase (SOD). Such agents, treatments and conditions can reduce or protect cardiomyocytes and populations of cardiomyocytes from cell death or apoptosis. Such agents may be at an effective concentration, for example, selenium at a concentration of 1 to 20 ng/ml, or 0.5 to 50 ng/ml; lithium at a concentration of 1 to 20 ng/ml, or 0.5-50 ng/ml; ascorbic acid or ascorbate at a concentration of 0.1 to 20 ug/ml, or 1 ug/ml; or superoxide dismutase (SOD) at a concentration of 1 to 100 u/ml, or 1 to 10 u/ml.

Methods for producing a cell culture of cardiomyocytes can include contacting mesoderm cells with a wingless-int-1 (Wnt) family member. In various aspects, a wingless-int-1 (Wnt) family member is Wnt-5a. Wingless-int-1 (Wnt) family members can be at an effective concentration, for example, Wnt-5a at a concentration of about 1 to 10 ng/ml.

Methods for producing a cell culture of cardiomyocytes, as well as cell populations of cardiomyocytes include expression of a marker associated with cardiomyocytes, at a given developmental, maturation or differentiation stage. Such cells may be progenitor or precursor cells of cardiomyocytes. In one embodiment, at least a portion of cells express Nkx2.5/Csx marker. In additional embodiments, at least a portion of cells express a GATA binding family transcription factor (GATA binding protein, such as GATA 4), MEF2 (Myocyte Enhancer Factor 2), HAND (heart and neural crest derivatives), Irx, Tbx, or HRT family of transcription factors, SRF (serum response factor), Isl1 (Islet1), LIM (named from the Lin-11, Isl-1 and Mec-3 genes) or alpha-actin marker.

Neural cells can be produced within the culture of cardiomyocytes or can be provided to the culture of cardiomyocytes by way of a separate culture of neural cells (e.g., pre-differentiated or primary neural cells or neural progenitor cells). In one embodiment, neural cells can be produced by addition of a retinoic acid receptor ligand to mesoderm cells. Exemplary non-limiting retinoic acid receptor ligand includes retinoic acid, for example, a concentration of 1-20 mMol, or 5-10 mMol retinoic acid. In another embodiment, cardiomyocyte formation is promoted by contact with neural cells for a period of time, for example, about 12-48 hours.

Endoderm cells can be produced within the culture of cardiomyocytes or can be provided to the culture of cardiomyocytes by way of a separate culture of endoderm cells (e.g. primary culture of endo-epithelial cells). In one embodiment, endoderm cells can be produced by addition of a BMP receptor ligand to mesoderm cells. In another embodiment, cardiomyocyte formation is promoted by contact with endoderm cells for a period of time, for example, about 12-48 hours.

Methods for producing a cell culture of cardiomyocytes can include contacting mesoderm cells with insulin; a thyroid hormone, or an insulin-like growth factor (IGF). Exemplary non-limiting insulin is a concentration of about 5 to 50 µg/ml, or about 15 µg/ml. Exemplary non-limiting thyroid hormone is a concentration of about 1 to 40 ng/ml, or about 20 ng/ml. A particular thyroid hormone includes T3/4. Exemplary non-limiting IGF is a concentration of about 5 to 50 ng/ml, or about 10 ng/ml. A particular IGF is IGF-1.

Exemplary non-limiting examples of FGF receptor ligand include FGF basic (FGF2, bFGF), acidic FGF (FGF1, aFGF), and combinations thereof. Exemplary non-limiting amounts (concentrations) of FGF is between about 2 to 200 ng/ml, or about 5 to 20 ng/ml.

Exemplary non-limiting examples of BMP receptor ligand include BMP4, BMP2, BMP7), and combinations thereof. Exemplary non-limiting amounts (concentrations) of BMP receptor ligand is between about 0.1 to 100 ng/ml, or about 0.5 to 10 ng/ml.

Methods for producing a cell culture of cardiomyocytes, as well as cell populations of cardiomyocytes include growth medium, which can be added or changed at any time, for a period of 1-60 minutes, 1-60 hours or 1-60 days. In exemplary embodiments, fresh growth media is added prior to, during or following a step of a method of the invention. In additional exemplary embodiments, fresh growth media is added to a cell culture of the invention at a given developmental, maturation or differentiation stage, or during cell expansion (proliferation).

Exemplary cell media for producing a cell culture of cardiomyocytes, as well as cell populations of cardiomyocytes include a stem cell media or a cardio cell media. Stem cell or a cardio cell media can include a basal media and one or more of supplements, such as human albumin, essential amino acids, non essential amino acids, L-glutamine, a thyroid hormone, insulin, transferrin, ethanolamine, sodium selenite, a hydrosoluble vitamin, a liposoluble vitamin or B27 supplement. Exemplary basal media includes DMEM, F12 or DMEM:F12 (e.g., in a ratio of about 1:1).

Methods for producing a cell culture of cardiomyocytes, as well as populations of cardiomyocytes that include non-beating contractile cardiomyoblasts are provided. Methods for producing a cell culture of cardiomyocytes, as well as populations of cardiomyocytes that include beating contractile cardiomyocytes are provided. Relative proportions or amounts of such cell types within cell cultures include 50%, 60%, 70%, 80%, 90% or more non-beating contractile cardiomyoblasts in a cell culture, as well as 50%, 60%, 70%, 80%, 90% or more beating contractile cardiomyocytes in a cell culture.

Beating (contractile) frequency of cardiomyocytes can be modulated by culture media pH, temperature, or a modulator drug. Exemplary non-limiting modulator drugs include catecholamine, a calcium channel blocker, or potassium.

Methods for producing a cell culture of cardiomyocytes, as well as populations of cardiomyocytes include contacting cardiomyocytes or contact of cardiomyocytes with a cardioplegic solution or treatment, and cardiomyocytes in a cardioplegic solution or treatment. Exemplary non-limiting cardioplegic solution or treatment (e.g., hypoxia) induces diastolic arrest of beating cardiomyocytes. Exemplary non-limiting cardioplegic solution or treatment (e.g., hypoxia) reduces energy requirement of beating cardiomyocytes. Exemplary non-limiting cardioplegic solution or treatment (e.g., hypoxia) inhibits hypoxia induced damage of contractile (beating) cardiomyocytes. Non-limiting cardioplegic solution includes a mixture of one or more of: KCl (10-20 mM); $MgCl_2$ (10 mM); $CaCl2$ (1.2 mM); puerarin (0.5 mM), or Nifedipine (1-10 uM). Non-limiting cardioplegic solution can also include a tris(hydroxymethyl)aminomethane or Hanks balanced salt solution adjusted to a pH of approximately 8.6). Non-limiting cardioplegic solution can further include a one or more of L-Monosodium Glutamate Monohydrate or L-Monosodium Aspartate Monohydrate, or a mixture of L-Monosodium Glutamate Monohydrate and L-Monosodium Aspartate Monohydrate, for example, about 3-5% (e.g., 4.277%) of L-Monosodium Glutamate Monohydrate with or without about 3-5% (e.g., 3.923%) of L-Monosodium Aspartate Monohydrate.

Methods for producing a cell culture of cardiomyocytes, as well as populations of cardiomyocytes that include isolating and isolated immature cardiomyocytes (cardioblasts) prior to beating (contractile activity) are provided. Methods for producing a cell culture of cardiomyocytes, as well as populations of cardiomyocytes that further include isolating and isolated mature contractile (beating) cardiomyocytes are also provided.

Methods for producing a cell culture of cardiomyocytes, as well as populations of cardiomyocytes include preserving and preserved cardiomyocytes. In various embodiments, preserving and preserved cardiomyocytes include freezing (frozen) or storing (stored) cardiomyocytes, such as, for example, cells having spontaneous and periodic electrical activity; immature cardiomyocytes (cardioblasts); nodal, sino-atrial or pacemaker cells; mature contractile cardiomyocytes; and mixed populations thereof.

Methods for producing a cell culture of cardiomyocytes, as well as populations of cardiomyocytes that include enriching and enriched, selecting and selected cardiomyocytes are provided. Cell cultures and methods for producing cell cultures by such methods include cells produced by a treatment that requires anaerobic metabolism so that cells unable to survive by anaerobic metabolism senesce or die are provided, thereby enriching for cells that survive via anaerobic metabolism. Cell cultures and methods for producing cell cultures by such methods include conditions of reduced oxygen (e.g., less than 2%), such as hypoxia, contact with lactic acid or contact with a cardioplegic solution or treatment.

Methods for producing a cell culture of cardiomyocytes, as well as populations of cardiomyocytes include enriching (enriched) or selecting (selected) cardiomyocytes of a selected developmental, maturation or differentiation stage are provided. In various non-limiting embodiments, a cardiomyocyte population includes nodal, sino-atrial or pacemaker cells, mature contractile cardiomyocytes, immature cardiomyocytes (cardioblasts), or a mixed population thereof. Cardiomyocytes of appropriate developmental, maturation or differentiation stage can be identified and removed or recovered. Recovering (recovered) or removing enriched or selected cardiomyocytes of appropriate developmental, maturation or differentiation stage are therefore included in the invention. Enriched or selected cardiomyocytes recovered or removed can be distributed in a cell culture dish, plate, vial, tube, flask or bottle. Enriched or selected cardiomyocytes that are recovered or removed can be frozen, for example, at −20 degrees C. or less, e.g., −70 degrees C.

In particular embodiments, a cell culture includes immature cardiomyocytes (cardiomyblasts), wherein 50% or more (e.g., 60%, 70%, 80%, 90%, etc.) of said culture comprises immature cardiomyocyte (cardiomyblast) cells. In additional particular embodiments, a cell culture includes immature cardiomyocytes (cardiomyblasts) in which no more than about 30% (e.g., no more than about 25%, 20%, 15%, 10%, 5%, etc.) of said cells beat or contract. In further particular embodiments, a cell culture includes a population of cells that are able to survive anaerobic conditions (e.g., an atmosphere of 0%-2% oxygen) for a period of time (e.g., 1-60 minutes or 1-8 hours). In a particular aspect, 75% or more of cardiomyocyte (e.g., immature cardiomyocyte (cardiomyblast)) cells survive anaerobic conditions for 30, 60 or more minutes. In another particular aspect, no more than about 25% (no more than about 20%, 15%, 10%, 5%, etc.) of cardiomyocyte (e.g., immature cardiomyocyte (cardiomyblast)) cells die when subjected to anaerobic conditions for 30, 60 or more minutes. Such embodiments include cell cultures of immature cardiomyocytes (cardiomyblasts) in which the immature cardiomyocyte (cardiomyblast) cells proliferate. Such embodiments further include cell cultures of immature cardiomyocytes (cardiomyblasts) in which no more than about 30% (no more than about 25%, 20%, 15%, 10%, 5%, etc.) of said immature cardiomyocyte (cardiomyblast) cells exhibit a function associated with contractile (beating) cardiomyocytes.

Cell cultures can be included in a container, or attached to a substrate. In a particular embodiment, a cell culture includes a substrate to which the cells are attached. Exemplary containers and substrates include tissue culture dishes or plates, glass or plastic slides, multiwell plates or dishes having disposed therein the cardiomyocyte (cardiomyblast) cells in one or more of said wells.

Cardiomyocytes, as well as populations of cardiomyocytes including enriched or selected cardiomyocytes of any developmental, maturation or differentiation stage thereof can be used to screen for or identify cardioactive agents. In various non-limiting embodiments, a cardiomyocyte population used in a screen or identification method includes nodal, sino-atrial or pacemaker cells, mature contractile cardiomyocytes, immature cardiomyocytes (cardioblasts), or a mixed population thereof.

In accordance with the invention, there are provided methods of screening and identifying cardioactive agents. In one embodiment, a method includes contacting a cardiomyocyte with a test agent; and determining if the test agent modulates an activity or function of cardiomyocytes within the population. A test agent modulating an activity or function of cardiomyocytes within the population identifies the test agent as a cardioactive agent. Exemplary activity or function that can be modulated include contraction or beating, or production of a metabolic product (e.g., production of one or more of urea, creatine or CO2), or intracellular enzyme (e.g., one or more of lactate dehydrogenase, creatine phosphokinase (CPK), creatine kinase (CK) or troponin), or cellular apoptosis, necrosis, death; or de-differentiation, maturation, or division.

Methods of screening and identifying cardioactive agents include those suitable for high throughput screening, which include arrays of cardiomyocyte cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., *Comb. Chem. High Throughput Screen.* 7:133 (2004)). For example, microarray technology has been extensively utilized to probe the interactions of thousands of genes at once, while providing information for specific genes (see, e.g., Mocellin and Rossi, *Adv. Exp. Med. Biol.* 593:19 (2007)).

Such high-throughput screening methods can identify cardioactive agents. For example, cardiomyocyte cells (e.g., cardiomyoblasts, cardiomyocytes or sino-atrial nodal cells) can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vectors.

Such high throughput methods are therefore also applicable to predictive toxicology. The use of cardiomyocyte cells (e.g., cardiomyoblasts, cardiomyocytes or sino-atrial nodal cells) positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for high-throughput or high content screening using small molecule libraries, siRNA libraries, adenoviral transfection vectors, and gene based microarray approaches can identify various therapeutic and cardiac liability targets. Such techniques also allow direct high-throughput measurement of cardiac intervention strategies by means of fluorescent reporter dyes and biomarkers for cell health and morphological phenotype, expression of fluorescent reporter proteins, various FRET approaches and direct measurement of electrophysiological currents in live cells.

Cardiomyocytes, as well as populations of cardiomyocytes including enriched or selected cardiomyocytes of any developmental, maturation or differentiation stage thereof can be used to treat a subject in need of increased numbers or function of cardiomyocytes. In one embodiment, a method for treating a subject in need of increased numbers or function of cardiomyocytes includes administering, delivering or transplanting into the subject a cardiomyocyte population of any developmental, maturation or differentiation stage thereof as set forth herein, optionally produced by any method as set forth herein. In another embodiment, a method for treating a subject in need of increased numbers or function of cardiomyocytes, includes grafting a cardiomyocyte population of any developmental, maturation or differentiation stage thereof as set forth herein, optionally produced by any method as set forth herein, into the heart of a subject.

The terms "subject" and "patient" are used interchangeably herein and refer to animals, typically mammals, such as humans, non-human primates (gorilla, chimpanzee, orangutan, macaque, gibbon), domestic animals (dog and cat), farm and ranch animals (horse, cow, goat, sheep, pig), laboratory and experimental animals (mouse, rat, rabbit, guinea pig). Subjects include disease model animals (e.g., such as mice, rats and non-human primates) for studying in vivo efficacy (e.g., a cardiac disease or disorder animal model). Human subjects include children, for example, newborns, infants, toddlers and teens, between the ages of 1 and 5, 5 and 10 and 10 and 18 years, adults between the ages of 18 and 60 years, and the elderly, for example, between the ages of 60 and 65, 65 and 70 and 70 and 100 years.

Subjects include mammals (e.g., humans) in need of treatment for a cardiac disease or disorder. Subjects also include those at risk of having a cardiac disease or disorder. Target subjects for treatment therefore include those having or at risk of having a cardiac disease or disorder.

Exemplary cardiac diseases and disorders included, but are not limited to, atherosclerosis, stroke, congenital heart disease, congestive heart failure, angina, myocarditis, coronary artery disease, cardiomyopathy, dilated cardiomyopathy, hypertrophic cardiomyopathy, endocarditis, myocardial infarction (Heart Attack), diastolic dysfunction, cerebrovascular disease, valve disease, high blood pressure (Hypertension), mitral valve prolapse and venous thromboembolism.

At risk subjects include those with a family history (high blood pressure, heart disease), genetic predisposition (hypercholesterolemia), or who have suffered a previous affliction with a cardiac disease or disorder. At risk subjects further include those with or at risk of high blood pressure or high cholesterol due to a genetic predisposition or a diet, such as high fat, or environmental exposure, such as smokers.

The doses or "amount effective" or "amount sufficient" in a method of treatment in which it is desired to achieve a therapeutic benefit or improvement includes, for example, any objective or subjective alleviation or amelioration of one, several or all pathologies, adverse symptoms or complications associated with or caused by the cardiac disease or disorder to a measurable or detectable extent. Thus, in the case of a cardiac disease or disorder, the amount will be sufficient to provide a therapeutic benefit to a given subject or to alleviate or ameliorate a pathology, adverse symptom or complication of the cardiac disease or disorder in a given subject. The dose may be proportionally increased or reduced as indicated by the status of treatment or any side effect(s).

In methods of treatment, a method may be practiced one or more times (e.g., 1-10, 1-5 or 1-3 times) per day, week, month, or year. The skilled artisan will know when it is appropriate to delay or discontinue administration. An exemplary non-limiting dosage schedule is 1-7 times per week, for 1, 23, 4, 5, 6, 7, 8, 9, 10, 15, 20 or more weeks, and any numerical value or range or value within such ranges.

Of course, as is typical for any treatment or therapy, different subjects will exhibit different responses to treatment and some may not respond or respond inadequately to a particular treatment protocol, regimen or process. Amounts effective or sufficient will therefore depend at least in part upon the disorder treated (e.g., the type or severity of the cardiac disease or disorder), the therapeutic effect desired, as well as the individual subject (e.g., the bioavailability within the subject, gender, age, etc.) and the subject's response to the treatment based upon genetic and epigenetic variability (e.g., pharmacogenomics).

The invention further provides kits, including cardiomyocytes, as well as populations of cardiomyocytes enriched or selected for any developmental, maturation or differentiation stage, packaged into suitable packaging material. In various non-limiting embodiments, a kit includes a cardiomyocyte population that includes nodal, sino-atrial or pacemaker cells, mature contractile cardiomyocytes, immature cardiomyocytes (cardioblasts), or a mixed population thereof. In various aspects, a kit includes instructions for using the kit components e.g., instructions for performing a method of the invention, such as culturing, expanding (increasing cell numbers), proliferating, differentiating, maintaining, or preserving cardiomyocytes, or a cardiomyocyte cell based therapy. In various aspects, a kit includes an article of manufacture, for example, an article of manufacture for culturing, expanding (increasing cell numbers), proliferating, differentiating, maintaining, or preserving cardiomyocytes, such as a tissue culture dish, tube, flask, roller bottle or plate (e.g., a single multi-well plate or dish such as an 8, 16, 32, 64, 96, 384 and 1536 multi-well plate or dish). In additional various aspects, a kit includes an article of manufacture, for example, an article of manufacture for delivering, introducing or transplanting cardiomyocytes into a subject locally, regionally or systemically.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, cardiomyocytes can be included in a tissue culture dish, tube, flask, roller bottle or plate (e.g., a single multi-well plate or dish such as an 8, 16, 32, 64, 96, 384 and 1536 multi-well plate or dish) together with instructions for culturing, expanding (increasing cell numbers), proliferating, differentiating, maintaining, or preserving cardiomyocytes. In an additional non-limiting example, cardiomyocytes can be included in a container, pack, or dispenser together with instructions for administration to a subject to treat a disease or disorder or cardiac tissue, such as atherosclerosis, stroke, congenital heart disease, congestive heart failure, angina, myocarditis, coronary artery disease, cardiomyopathy, dilated cardiomyopathy, hypertrophic cardiomyopathy, endocarditis, myocardial infarction (Heart Attack), diastolic dysfunction, cerebrovascular disease, valve disease, high blood pressure (Hypertension), mitral valve prolapse and venous thromboembolism. Instructions may additionally include indications of a satisfactory clinical endpoint or any adverse symptoms or complications that may occur, storage information, expiration date, or any information required by regulatory agencies such as the Food and Drug Administration for use in a human subject.

The instructions may be on "printed matter," e.g., on paper or cardboard within the kit, on a label affixed to the kit or packaging material, or attached to a tissue culture dish, tube, flask, roller bottle, plate (e.g., a single multi-well plate or dish such as an 8, 16, 32, 64, 96, 384 and 1536 multi-well plate or dish) or vial containing a component (e.g., cardiomyocytes) of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include cell growth medium, buffering agent, a preservative, or a cell stabilizing agent. Each component of the kit can be enclosed within an individual container or in a mixture and all of the various containers can be within single or multiple packages.

Cardiomyocytes, as well as populations of cardiomyocytes including enriched or selected cardiomyocytes of any developmental, maturation or differentiation stage thereof can be packaged in dosage unit form for administration and uniformity of dosage. "Dosage unit form" as used herein refers to physically discrete units suited as unitary dosages; each unit contains a quantity of the composition in association with a desired effect. The unit dosage forms will depend on a variety of factors including, but not necessarily limited to, the particular composition employed, the effect to be achieved, and the pharmacodynamics and pharmacogenomics of the subject to be treated.

Cardiomyocytes as well as populations of cardiomyocytes including enriched or selected cardiomyocytes of any developmental, maturation or differentiation stage thereof and methods of the invention can be included in or employ pharmaceutical formulations. Pharmaceutical formulations include "pharmaceutically acceptable" and "physiologically acceptable" carriers, diluents or excipients. The terms "pharmaceutically acceptable" and "physiologically acceptable" mean that the formulation is compatible with pharmaceutical administration. Such pharmaceutical formulations are useful for treatment of, or administration or delivery to, or transplant into, a subject in vivo or ex vivo.

Pharmaceutical formulations can be made to be compatible with a particular local, regional or systemic administration or delivery route. Thus, pharmaceutical formulations include carriers, diluents, or excipients suitable for administration by particular routes. Specific non-limiting examples of routes of administration for compositions of the invention are parenteral, e.g., intravenous, intraarterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

The term "contacting," when used in reference to cells or a cell culture or method step or treatment, means a direct or indirect interaction between the composition (e.g., cell or cell culture) and the other referenced entity. A particular example of a direct interaction is physical interaction. A particular example of an indirect interaction is where a composition acts upon an intermediary molecule which in turn acts upon the referenced entity (e.g., cell or cell culture).

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, Genbank accession numbers and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to a "cardiomyocyte" includes a plurality of cardiomyocytes, and reference to "a cell culture" can include multiple cell types of varied developmental, maturation or differentiation stage within the culture.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes any numerical value or range within or encompassing such values, such as 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and any numerical range within such a range, such as 90-92%, 90-95%, 95-98%, 96-98%, 99-100%, etc. In an additional example, reference to greater or less than a particular percent, e.g., greater than 25% means 26%, 27%, 28%, 29%, 30%, 31%, . . . etc.; and less than 25% means 24%, 23%, 22%, 19%, 18%, 17%, . . . etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example is of an exemplary protocol for obtaining a mixed cardiomyocyte population.
1. One passage before differentiation, stem cells are plated in deep dishes which can carry 1-3 cm of supernatant. Stem cells are fed according to hES cells protocols.
2. Incubator set to 37-37.5° C., 2-5% O2 5-6% CO2 and 98% H2O. Stem cells are overgrown in the original plated dishes: deep dishes (5-10 mm of supernatant) for increasing media volume will ensure hypoxia and enough nutriments for cellular overgrowth. The culture will stabilize after 3-5 days of overgrowth.
3. Day 1-3 addition of retinoic acid (RA) 5 mM in DMSO to final concentration of 5 µM
4. Day 1 to the end of the protocol. BMP4 10 ng/ml
5. Day 1 to the end of the protocol FGF—10 ng/ml
6. Replace the media daily up to day 10 and than every other day
7. At day 20-25 first colonies with beating clumps and typical morphology
8. Day 28. The cells are incubated for 1-2 hour in a 50% cardioplegic solution with lactic acid, protection, and absolute hypoxia (media is degassed in vacuum and flushed with nitrogen for 1 hour, the incubator is set for 0% oxygen or flushed completely with nitrogen). The cardiomyocytes will switch to a reduced anaerobic metabolism: LDH/lactic acid. The rest of the cells will die. After 1 hour the cardioplegic solution is removed and the cells are resuscitated with regular media.
9. Day 29 Death cells are removed. The purification procedure is repeated if needed.
10. Day 30. The cells are incubated for 2-5 minutes with a mixture of cardioplegic solution 50% v/v with a dissociation enzyme (for example trypsin 0.25%). The cells are re-plated on a fresh substrate with the same surface (1:1).
11. In the next days, the feeding is continued with Cardio-Media plus FGF and membrane stabilizer (Puerarin)
12. The culture is passaged again when confluence is reached, using the combination of the cardioplegic solution and dissociation enzyme.

Example 2

This example is of an exemplary protocol for obtaining early purified cardiomyocyte population.
1. One passage before differentiation the stem cells are plated in deep dishes which can carry 2-3 cm of supernatant. Stem cells are fed according to hES cells protocols.
2. Stem cells are overgrown in the original plated dishes until layering of the colonies is observed (by the yellowish color on the surface) and the media is increased in volume to ensure hypoxia and nutriments. The culture will stabilize after 3-5 days of overgrowth
3. In a separate dish a pre-differentiated culture consisting of pax6/nestin positive active dividing cells of 50,000 cells/cm2, will incubate overnight the CardioMedia. Next day the media is collected and filtered. The culture can be obtained from primary culture of neural stem cells or by differentiating human embryonic stem cells for 5-7 days in a serum free media which contains 10 uM of retinoic acid and 5 ng/ml FGF2 added daily at feeding.
4. The collected media from the neural culture is supplemented with 10 ng/ml BMP4 and 5 ng/ml bFGF and is used to feed the cardio cultures.
5. The cultures are fed every day. A mixture of some endodermal and mostly mesodermal population is observed in 3-5 days.
6. Replace media every other day after day 10.
7. At day 28, perform the purification method described in the above example
8. Dissociate cultures at day 30 and re-plate (1:1)
9. Feed with non-conditioned media plus FGF and membrane stabilizers
10. Passage the cultures when confluents Example 3

This example includes a description of media compositions used in examples 1 and 2. Cardio Media includes DMEM:F12 LO, B27 supplement, MEM-NE Aminoacids 1×, Glutamax 1×, Ascorbic acid 20 µg/ml, thyroid hormones T3/4 20 ng/ml and insulin 10 ug/ml Cardioplegic solution includes THAM buffer (thrometamine) 0.3 Mol, KCl 10 mM, Puerarin 0.5 mM, L-Monosodium Glutamate Monohydrate 4%, L-Monosodium Aspartate Monohydrate 4%, Trehalose 0.25%, Lactic Acid 2 mM and Ascorbic acid 20 µg/ml. Resuscitation media includes Cardio Media, Puerarin 0.5 mM, Trehalose 0.25% and Superoxide dismutase.

Neural media includes DMEM:F12 high glucose, B27 Supplement 1×, MgCl 0.5 mM, insulin 10 ug/ml, selenite 5 ng/ml and transferrin 20 ug/ml.

Example 4

This example includes a description of results.

Differentiation of mesodermal cells occurs shortly after some patches of ectodermal colonies are observed. The mesodermal cells typically surround an ectodermal cluster. The first sign of cardiomyocyte differentiation is the formation of trabecular clusters with cells reassembling syncitial structures. The trabecules of syncitial cardiomyocytes are radial distributed around the ectodermal center and will start mechanical activity around days 20-25 of differentiation. If arrested from mechanical activity, the cardiac tissue will continue cellular division (hyperplasia). If let to continue beating, cell volume will increase, cells will fuse in syncitial structures and will terminally differentiate (hypertrophya). (FIG. 2) Three types of cardiac cells are present in early development, nodal cells, contractile cardiomyocytes and noncontractile undifferentiated cells.

Nodal cells are immature cardiomyocytes: small cells with membrane ionic "leakage" and periodic spontaneous depolarization at threshold (pacemaker cells).

Contractile cardiomyocytes have muscular characteristics (actin filaments and gap junctions) and are organized in syncitial mixoma like structures.

Noncontractile, undifferentiated cells are typically actively dividing, with potential to generate nodal and contractile cells.

Cardiac cells are typically identified by detecting at least two of cardiac markers. Particular non-limiting examples include Nkx2.5/Csx, which is first expressed in the presumptive precardiac mesoderm; transcription factors such as a GATA binding family transcription factor (GATA binding protein, such as GATA 4), MEF2, HAND, Irx, Tbx, and HRT; SRF; LIM; and alpha-actin.

Example 5

This example includes a description of characterization of cardiomyocytes generated from human embryonic stem cells.

The human embryonic stem cell cultures were expanded in 75 cm2 cell culture flasks and underwent the same differentiation methods described in Example 1. The cultures were then exposed to cardioplegic solution and grown for another week. Samples were plated in imaging chambers (Nunc) and characterization was performed using antibodies against the transcription factor NKX2.5 and a-actin. FIG. 3 illustrates the cells.

In brief, FIG. 3A illustrates extensive (hyperplasic) and homogenous growth of cardiomyoblasts in a 18 day old culture showing formation pf trabecular clusters (4×). FIG. 3B illustrates syncitial structures (arrows) organizing after 21-24 days of differentiation. If contractile activity is arrested cells continue to grow in the form of high density, hyperplasic cultures (A) (20×). FIGS. 3C)-3E) illustrate cardiomyocyte cultures dissociated and replated on adherent substrate at earlier stages, when NKX2.5 transcription factor is present (C) (D—Nuclear staining with bisbenzimide; E—merged pictures). This marker is characteristic for myocardial and endocardial tissue (100×). FIGS. 3F)-3H) illustrate more mature myocardial cells fuse and form trabecular structures positive for a-actin (F) (G—bisbenzimide nuclear stain, H—merged picture). The actinic expression coincides with the initiation of mechanical activity. If cardioplegic media is used the syncitial agglomerates do not loose the positivity for actin, however maturation is delayed (60×). FIGS. 3I)-3K) illustrate actin labeling is persistent (I) even after enzymatic dissociation of the cultures (J—nuclear stain with bisbenzimide, K—Merged picture (20×)). FIGS. 3L)-3N) illustrate colabeling with NKX2.5 (L) and actin (M) showing the overall expression of the NKX2.5, while the actin is progressively expressed (N—Nuclear counterstain (100×)).

BIBLIOGRAPHY

1. Bram van Wijka, Antoon F. M. Moormana and Maurice J. B. van den Hoff-Role of bone morphogenetic proteins in cardiac differentiation. Cardiovasc Res. 2006 Nov. 21, in press
2. Chen, Di, Zhao, Ming, and Mundy, Gregory R. "Bone Morphogenetic Proteins". Growth Factors 22 (4), 2004: 233-241.
3. Increased cardiomyocyte differentiation from human embryonic stem cells in serum-free cultures. Passier R, Oostwaard D W, Snapper J, Kloots J, Hassink R J, Kuijk E, Roelen B, de la Riviere A B, Mummery C. Stem Cells. 2005 June-July; 23(6):772-80
4. Kenneth R. Boheler, Jaroslaw Czyz, David Tweedie, Huang-Tian Yang, Sergey V. Anisimov, Anna M. Wobus. Differentiation of Pluripotent Embryonic Stem Cells Into Cardiomyocytes. Circulation Research. 2002; 91:189.
5. Mohsen Hosseinkhani, Hossein Hosseinkhani, Ali Khademhosseini, Fiona Bolland, Hisatoshi Kobayashi, Susanna Prat Gonzalez. Bone morphogenetic protein-4 enhances cardiomyocyte differentiation of cynomolgus monkey ES cells in Knockout Serum Replacement medium. Embryonic Stem Cells (in press)
6. Shinsuke Yuasa, Yuji Itabashi, Uichi Koshimizu, Tomofumi Tanaka, Keijiro Sugimura, Masayoshi Kinoshita, Fumiyuki Hattori, Shin-ichi Fukami, Takuya Shimazaki, Hideyuki Okano, Satoshi Ogawa & Keiichi Fukuda. Transient inhibition of BMP signaling by Noggin induces cardiomyocyte differentiation of mouse embryonic stem cells. Nature Biotechnology 23, 607-611 (2005)
7. Yu Chen, Ivo Amende, Thomas G. Hampton, Yinke Yang, Qingen Ke, Jiang-Yong Min, Yong-Fu Xiao, and James P. Morgan. Vascular endothelial growth factor promotes cardiomyocyte differentiation of embryonic stem cells. Am J Physiol Heart Circ Physiol 291: H1653-H1658, 2006.
8. Christine Mummery, Dorien Ward-van Oostwaard, Pieter Doevendans, Rene Spijker, Stieneke van den Brink, Rutger Hassink, Marcel van der Heyden, Tobias Opthof, Martin Pera, Aart Brutel de la Riviere, Robert Passier, and Leon Tertoolen. Differentiation of Human Embryonic Stem Cells to Cardiomyocytes. Role of Coculture With Visceral Endoderm-Like Cells. Circulation 2003; 107:2733.
9. Catherine A. Risebro, Nicola Smart, Laurent Dupays, Ross Breckenridge, Timothy J. Mohun and Paul R. Riley. Hand1 regulates cardiomyocyte proliferation versus differentiation in the developing heart. Development 133, 4595-4606 (2006)
10. C Mummery, D Ward-van Oostwaard, P Doevendans, R Spijker, S van den Brink, R Hassink, M van der Heyden, T Opthof, M Pera, A B de la Riviere, R Passier, L Tertoolen. Differentiation of human embryonic stem cells to cardiomyocytes: role of coculture with visceral endoderm-like cells. Circulation (2003) 107: 2733-40.
11. C Mummery, D Ward, C E van den Brink, S D Bird, P A Doevendans, T Opthof, A Brutel de la Riviere, L Tertoolen, M van der Heyden, M Pera. Cardiomyocyte differentiation of mouse and human embryonic stem cells. J Anat (2002) 200: 233-42.
12. Koshiro Monzen, Ichiro Shiojima, Yukio Hiroi, Sumiyo Kudoh, Toru Oka, Eiki Takimoto, Doubun Hayashi, Toru Hosoda, Akemi Habara-Ohkubo, Takashi Nakaoka, Toshiro Fujita, Yoshio Yazaki, and Issei Komuro. Bone Morphogenetic Proteins Induce Cardiomyocyte Differentiation through the Mitogen-Activated Protein Kinase Kinase Kinase TAK1 and Cardiac Transcription Factors Csx/Nkx-2.5 and GATA-4. Mol Cell Biol. 1999 October; 19(10): 7096-7105.
13. Jun K. Yamashita, Makoto Takano, Mina Hiraoka-Kanie, Chikashi Shimazu, Yan Peishi, Kentoku Yanagi, Akiko Nakano, Emi Inoue, Fumiyo Kita and Shin-Ichi Nishikawa. Prospective identification of cardiac progenitors by a novel single cell-based cardiomyocyte induction. The FASEB Journal. 2005; 19:1534-1536
14. Foshay, K., Rodriguez, G., Hoel, B., Narayan, J., Gallicano, G. I. "JAK2/STAT3 controls cardiomyocyte differentiation in vitro." Stem Cells 23 (2005): 530-543.
15. Yoshinori Ohtsu; Kohei Johkura; Ken-ichi Ito; Tomohiro Akashima; Kazuhiko Asanuma; Naoko Ogiwara; Toru Oka; Issei Komuro; Katsunori Sasaki; Jun Amano. Stimulation of P19CL6 With Multiple Reagents Induces Pulsating Particles In Vivo. Current Medical Research and Opinion Volume 22, Number 4
16. Hong Wei, Ondrej Juhasz, Jinliang Li, Yelena S. Tarasova, Kenneth R. Boheler. Embryonic stem cells and cardiomyocyte differentiation:phenotypic and molecular analyses
17. Wobus A. M.; Kaomei G.; Shan J.; Wellner M. C.; Rohwedel J.; Guanju J.; Fleischmann B.; Katus H. A.; Hescheler J.; Franz W. M. Retinoic Acid Accelerates Embryonic Stem Cell-Derived Cardiac Differentiation and Enhances Development of Ventricular Cardiomyocytes: Journal of Molecular and Cellular Cardiology, Volume 29, Number 6, 1997, pp. 1525-1539(15).

What is claimed is:

1. A method for producing a culture of cardiomyocytes, comprising:
   A) Providing a culture of stem cells that are at least 90% confluent or the cells have overgrown to form multiple layers of cells, or proliferating stem cells until the cells are at least 90% confluent or the cells have overgrown to form multiple layers of cells;
   B) Inducing formation of mesoderm by contacting the overgrown stem cells with a bone morphogenic protein (BMP) receptor ligand and an fibroblast growth factor (FGF) receptor ligand for a period of about 2 to 15 days; and
   C) promoting cardiomyocyte formation by contacting mesoderm cells with neural cells, or a neural cell conditioned culture supernatant, for a period of about 1 to 21 days, thereby producing a culture of cardiomyocytes.

2. The method of claim 1, wherein the cardiomyocytes comprise a population of cells comprising cells having spontaneous and periodic electrical activity.

3. The method of claim 2, wherein the cells having spontaneous and periodic electrical activity comprise nodal, sinoatrial or pacemaker cells; immature cardiomyocytes (cardiomyoblasts); mature contractile cardiomyocytes; or a mixed population thereof.

4. The method of claim 1, wherein the stem cells of step A) comprise a cell monolayer with 100% or more confluency.

5. The method of claim 1, wherein the stem cells of step A) form a multilayer culture.

6. The method of claim 1, wherein the stem cells of step A) have a density of about 150,000 to about 250,000 cells/cm 2.

7. The method of claim 1, wherein step B) further comprises addition of an acid.

8. The method of claim 7, wherein the acid comprises lactic, citric, fumaric, ascorbic, folic, malic, succinic, oxalacetic, or ketoglutaric acid.

9. The method of claim 1, wherein step B) further comprises subjecting the mesoderm cells to hypoxia.

10. The method of claim 1, wherein the stem cells, mesoderm cells or cardiomyocytes are subjected to an oxygen concentration of about 0.5 to 2.0%.

11. The method of claim 1, wherein step B) further comprises addition of an agent that inhibits cell death or apoptosis.

12. The method of claim 11, wherein the agent comprises selenium, lithium; ascorbic acid or ascorbate or superoxide dismutase (SOD).

13. The method of claim 12, wherein the selenium comprises sodium selenite.

14. The method of claim 12, wherein the selenium is at a concentration of 1 to 20 ng/ml, or 0.5 to 50 ng/ml.

15. The method of claim 12, wherein the lithium comprises lithium carbonate.

16. The method of claim 12, wherein the lithium is at a concentration of 1 to 20 ng/ml, or 0.5-50 ng/ml.

17. The method of claim 12, wherein the ascorbic acid or ascorbate comprises sodium or calcium ascorbate.

18. The method of claim 12, wherein the ascorbic acid or ascorbate is at a concentration of 0.1 to 20 ug/ml, or 1 ug/ml.

19. The method of claim 12, wherein the superoxide dismutase (SOD) is at a concentration of 1 to 100 u/ml, or 1 to 10 u/ml.

* * * * *